United States Patent
Clarke et al.

(10) Patent No.: US 6,740,191 B2
(45) Date of Patent: May 25, 2004

(54) THROUGH-TRANSMISSION WELDING OF CATHETER COMPONENTS

(75) Inventors: Gerry Clarke, Galway (IE); Gerard M. O'Connor, Galway (IE); Richard Sherlock, Galway (IE); Alan O'Driscoll, Brighton, MA (US); Cathal McNamara, Santa Rosa, CA (US); Hubert McDonagh, Galway (IE)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/791,887

(22) Filed: Feb. 22, 2001

(65) Prior Publication Data

US 2002/0115963 A1 Aug. 22, 2002

(51) Int. Cl.⁷ .................. A61M 29/00; B32B 31/24
(52) U.S. Cl. ............... 156/272.8; 156/8 C; 156/293; 156/308.2; 604/103
(58) Field of Search ............... 604/103; 156/272.8, 156/293, 294, 308.2, 86, 275.5

(56) References Cited

U.S. PATENT DOCUMENTS

| | | |
|---|---|---|
| 3,528,869 A | 9/1970 | Dereniuk |
| 3,769,117 A | 10/1973 | Bowen et al. |
| 4,069,080 A | 1/1978 | Osborne |
| 4,251,305 A | 2/1981 | Becker et al. |
| 4,636,609 A * | 1/1987 | Nakamata ............ 219/121 |
| 4,958,634 A | 9/1990 | Jang |
| 5,195,969 A | 3/1993 | Wang et al. |
| 5,267,959 A | 12/1993 | Forman |
| 5,501,759 A | 3/1996 | Forman |
| 5,795,332 A | 8/1998 | Lucas et al. |
| 5,893,959 A * | 4/1999 | Muellich .......... 156/272.8 |
| 5,961,765 A | 10/1999 | Kastenhofer |
| 6,027,477 A | 2/2000 | Kastenhofer |
| 6,136,258 A | 10/2000 | Wang et al. |
| 6,139,525 A | 10/2000 | Davis-Lemessy et al. |
| 6,165,166 A | 12/2000 | Samuelson et al. |

FOREIGN PATENT DOCUMENTS

| | | |
|---|---|---|
| GB | 2286147 | 8/1995 |
| WO | WO 00/26008 | 5/2000 |
| WO | WO 00/66345 | 10/2000 |
| WO | WO 00/58074 | 11/2000 |

OTHER PUBLICATIONS

SEBRA® Radio Frequency PIRF™ Plastic Welding and Forming, brochure from SEBRA, Tucson, AZ, Jan. 1991.
PIRF™ Catheter Manufacturing Equipment, brochure from SEBRA, Tucson, AZ, Jan. 1992.
ASUKA™ 2.9 F OTW PTCA balloon catheter, brochure from Schneider (Europe) AG, Feb. 1994.

* cited by examiner

*Primary Examiner*—Jeff H. Aftergut
*Assistant Examiner*—John T. Haran
(74) *Attorney, Agent, or Firm*—Sterne, Kessler, Goldstein & Fox P.L.L.C.

(57) ABSTRACT

A process for forming a heat weld between a catheter shaft and a surrounding balloon comprises selecting an elongate catheter shaft formed of thermoplastic polymeric material that is opaque to red and near-infrared light, and selecting a balloon formed of thermoplastic polymeric material that is transparent or translucent to red and near-infrared light. While a neck of the balloon is fitted in close contact around a distal portion of the catheter shaft, a laser beam of red and near-infrared light is applied through the balloon neck to impinge on the underlying opaque distal shaft, which is heated thereby. Heat from the shaft is conducted into the surrounding balloon neck so that adjacent annular portions of both components melt and mix. The molten materials are allowed to cool, forming a secure weld joint between the neck and the shaft. The process yields strong, flexible bonds between balloons and catheter shafts that may be selected from a wide variety of materials.

10 Claims, 4 Drawing Sheets

THROUGH-TRANSMISSION WELDING OF CATHETER COMPONENTS

FIELD OF THE INVENTION

This invention relates to welding components of catheters and more particularly to welding balloons to catheters. Bonds provided by such welding must provide mechanical strength, lateral flexibility, and resistance to hydraulic leakage under high pressures.

BACKGROUND OF THE INVENTION

Balloon catheters are used in the treatment of narrowings in tubular passageways of the human body, especially arterial obstructions, which are generally referred to as occlusions or stenoses. In particular, balloon catheters are used in procedures such as coronary angioplasty, peripheral angioplasty, drug delivery and stent delivery. During such procedures, a slender tubular catheter is threaded through the patient's passageways until the remote, or distal end of the catheter reaches the treatment site. Fluid injected into the external, proximal end of the catheter flows through a hollow lumen to reach and expand a balloon mounted to the distal end of the catheter. The fluid pressure used is varied as required to open the narrowing with the balloon, deliver the stent or delivery a drug at the treatment site.

Construction of a balloon catheter typically requires mounting of a separately molded balloon to the distal end of the catheter. Such balloons have a generally cylindrical dilating portion with conical ends tapering to shorter, smaller diameter, cylindrical necks that fit closely around the distal portion of the catheter where they are attached. The dilating portion of the balloon is made as thin as possible to achieve the lowest possible profile when the deflated balloon is wrapped around the catheter, and excellent flexibility of the assembly for negotiating tortuous passageways, while maintaining a reliable burst pressure for the intended medical application. Historically, balloons have been formed of a thermoplastic polymeric material that is optically transparent to facilitate viewing air bubbles that are flushed out with inflation liquid as the catheter is prepared for use. These balloons are typically blow-molded radially outward from extruded tubing so that the cone portions, and especially the mounting necks, are thicker and less flexible than the larger diameter dilating portion. However, several balloon-making processes have been developed to provide cones and necks that are about as thin as the dilating portion of the balloon. Such ultra-thin necks are especially susceptible to thermal damage if heat welding is used to attach the balloon to the catheter.

When the balloons are bonded using adhesive between the necks and the catheter, the increased stiffness in this area can reduce the ability of the catheter to track through tight bends. Historically, the solution to this design problem has been to make the balloon necks and/or the bond lengths as short as possible because shorter stiff sections have a reduced effect on catheter trackability. Further improvements to the flexibility of balloon bonds included welding, or melt-bonding the balloon necks to the catheter. While welding improves the joint flexibility compared to the use of adhesives, it brings about new difficulties, including the sufficient control of heat to create a satisfactory bond without damaging the surrounding structure. The most significant damage caused by poorly controlled welding heat is stiffening of the balloon cones resulting from crystallization, which is a loss of desirable molecular orientation achieved during stretch blow-molding of the balloon. Thermal control is especially difficult in small balloon catheters such as those used in the treatment of coronary artery disease.

A known approach to heat bonding balloons is to place a section of heat-shrink tubing around the neck to be bonded, then to shrink the tubing by applying hot air. The heating not only shrinks the tubing to apply pressure to the assembly, but the shaft and balloon neck are also melted together. During this process, the cone portion and remainder of the balloon must be carefully insulated to avoid heat damage.

Another known method for welding balloons to catheters is to advance the assembled catheter shaft and the neck of the balloon into a heated mold having a tapered bore to compress the neck against the shaft during bonding. A low-mass mold may be quickly heated and cooled using radio frequency energy. A disadvantage of this process is that very thin balloon necks may peel back as the assembly moves into the mold.

Another known welding approach for dilatation balloon bonding uses laser energy focused in the area where the bond is desired, on the annular interface between the balloon neck and the catheter shaft. This narrowly focused energy solves the heat control problem, but the process requires the materials of both the catheter and balloon to have the same high absorptivity for the particular energy emitted by the laser source, which is in the far-infrared range. Thus, the designer's choice of materials is limited. Alternatively, the known welding process may use a laser source having a wavelength in the red and near-infrared range, while still using balloon and catheter materials that were selected to strongly absorb far-infrared energy. This optional red and near-infrared energy is not well absorbed by the balloon and shaft materials in the bond area. To overcome this poor energy absorption, a component that is absorptive of red and near-infrared energy is placed in the bonding interface site between the balloon neck and catheter. The additional element absorbs energy sufficiently to melt the adjacent neck and shaft polymers, creating the weld. Thus, the known laser process solves some of the heat control problems in balloon welding, but requires a limited selection of particular pairs of polymers and, alternatively, the use of an extra weld element made of a material that is different from these particular polymer pairs.

OBJECTS OF THE INVENTION

It is an object of the present invention to provide a process for welding dilatation balloons to catheters with good control of the heat required.

Another object of the invention is to weld very thin balloon necks to an underlying catheter shaft with minimal thermal damage to portions of the balloon adjacent to the weld.

Another object of the invention is to provide a balloon angioplasty catheter wherein the balloon is welded to the catheter shaft, and the selection of polymer materials is broader than previously known for laser welded assemblies.

BRIEF DESCRIPTION OF THE INVENTION

In accordance with the present invention, a balloon catheter and process for making said catheter are provided. The catheter comprises a slender, elongate, tubular, flexible shaft having proximal and distal ends and at least one lumen extending from the proximal end to the distal end. The balloon is specially designed to be mounted onto the distal end of the catheter shaft, and to be inflated in conformance with tubular passageways in the human body. The balloon has a generally cylindrical dilating portion with conical ends tapering to shorter, smaller diameter, cylindrical necks that fit closely around the distal portion of the catheter shaft where the necks are attached. Through-transmission welding is used to attach at least one balloon neck to the catheter shaft, thus providing a short, strong, leak-proof bond that adds minimal bending stiffness to the catheter assembly. The welding process includes the following steps:

a. mounting a balloon formed of a transparent or translucent thermoplastic polymer around the distal end of a catheter shaft formed of opaque thermoplastic polymer;

b. transmitting laser energy in the red and near-infrared wavelength range through a portion of the balloon neck to the underlying catheter shaft causing both polymers to melt in a cylindrical zone that includes the annular interface between the neck and shaft; and c. permitting the molten polymers to cool, forming a solid weld joint.

The balloon may be formed from any thermoplastic polymer that is suitable for making catheter balloons and is transparent or translucent to energy in the red and near-infrared range. The catheter shaft may be formed from any material that is suitable for catheter construction and is opaque to the red and near-infrared energy range. Alternatively, the distal region of the catheter shaft may be made from a multi-layer coextrusion wherein only the outer layer needs to be opaque to the red and near-infrared energy range. Coextruded shaft construction offers further design flexibility, such as the use of a very low friction polymer for an inner layer, which may form a guidewire lumen. The energy directed toward the desired bond area is transmitted through the balloon neck without being absorbed significantly. It is the underlying catheter shaft, and particularly the outer shaft surface that absorbs the energy and rises in temperature. During the process, heat is conducted from the shaft such that both adjacent members melt in the weld area.

The preferred generator of red and near-infrared energy may be either a continuous ND:YAG laser, or a low power diode laser, either source having the following characteristics: a wavelength of 630–1580 nm; a spot size of approximately 580 micron (0.023 inches) diameter; and a power level of approximately 0.6–0.8 watts.

To obtain a short, annular weld between the balloon neck and the catheter shaft, it is preferred to have rotational relative motion between the assembled components and the energy source, most preferably by rotating the balloon and shaft combination about a central axis beneath a laser beam. Other relative motion processes are also possible, including processes which will form a short, helical, beam pattern within the desired annular bond area.

Thus, in accordance with the present invention, a balloon catheter is provided wherein the balloon is welded securely, yet flexibly to the catheter shaft, and the selection of polymer materials for both the balloon and the shaft is broader than previously known for laser welded assemblies. Any mutually heat bondable thermoplastic polymers may be selected, with the only limitations being that the balloon material is transparent or translucent and the shaft material is opaque, each with respect to red and near-infrared light. The balloon and shaft materials do not need to have matching, high absorptivity of far-infrared energy.

Another advantage of the invention is that very thin balloon necks can be welded to the catheter shaft with minimal damage to the necks or to the cone portions of the balloon because the laser beam can be transmitted through the transparent or translucent balloon material with little or no absorption of the welding energy.

BRIEF DESCRIPTION OF THE DRAWINGS

The invention will be further described, by way of examples, with reference to the accompanying drawings, wherein.

DESCRIPTION OF THE ILLUSTRATIVE EMBODIMENTS

The following description will be specifically provided in the context of coronary angioplasty dilatation catheters, the invention is not so limited and is applicable to other catheter assemblies and procedures. For example, it will be understood that the present invention also applies to balloon catheters used for peripheral angioplasty, drug delivery, stent delivery and the like.

Figure 1:
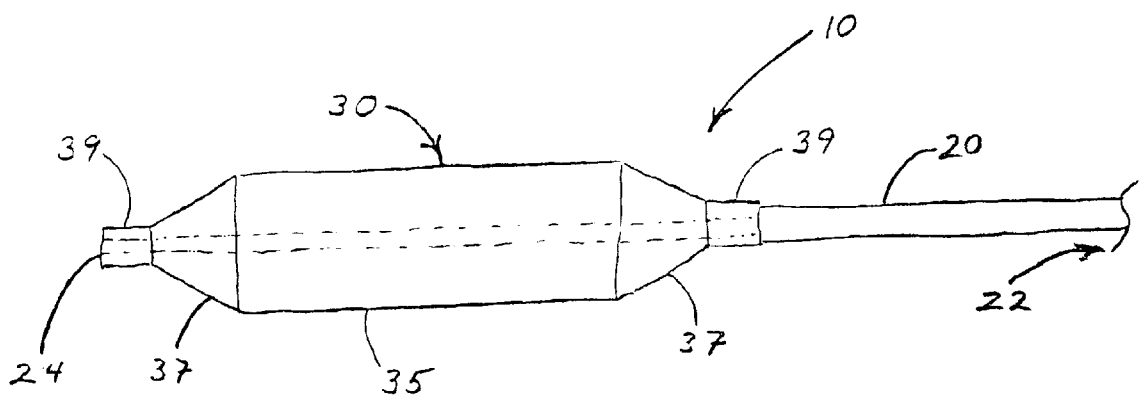
FIG. 1 is a side view of the distal region of a balloon catheter of the present invention.
Figure 2:
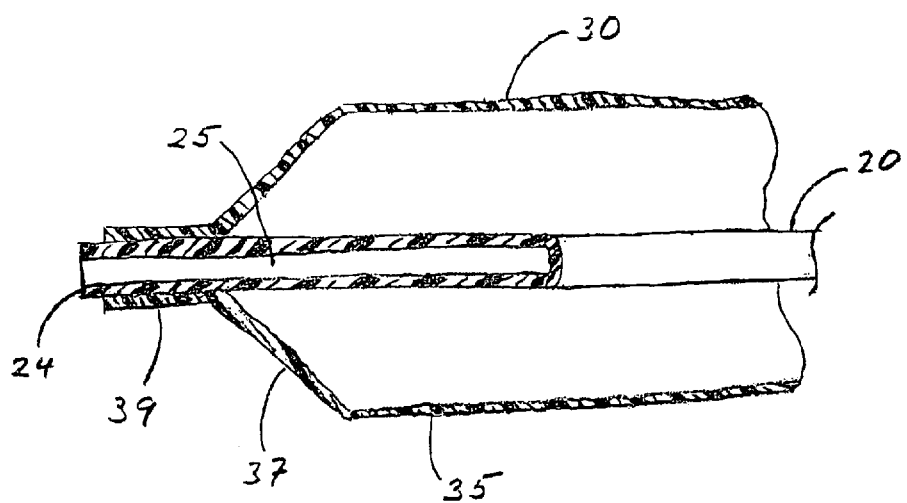
FIG. 2 is a longitudinal sectional view of the catheter of FIG. 1.

FIGS. 1 and 2 show the distal portion of balloon angioplasty catheter 10. The balloon catheter comprises an elongated, flexible catheter shaft 20 having a proximal end 22 and a distal end 24. A balloon member 30 is disposed near distal end 24 of catheter shaft 20. Balloon 30 comprises generally cylindrical dilating portion 35 having conical ends 37 tapering to shorter, smaller diameter, cylindrical necks 39 that fit closely around the distal portion of catheter shaft 20 where they are attached. Balloon 30 may be inflated and deflated through a lumen formed in the catheter shaft, which passageway is not shown. Catheter shaft 20 of the illustrative embodiment includes guidewire lumen 25, which extends from distal end 24 through the shaft portion within balloon 30 or farther in the proximal direction, and which may optionally extend the full length of the catheter. The portion of catheter shaft 20 within the proximal balloon neck has two lumens, not shown, which are arranged either coaxially or side-by-side. Thus, the proximal neck joint will usually be larger in diameter than the distal joint, as is well known in the art of balloon dilatation catheters. Although both necks 39 of balloon 30 need to be attached to catheter shaft 20, and both necks can be welded according to the invention, the description of the invention will focus primarily on the distal balloon neck merely for simplicity.

An alternative construction utilizes the inventive welding process in a so-called "fixed wire" PTCA catheter, wherein the balloon is mounted to a steerable guidewire. In such a device, a guidewire lumen is not necessary, so there is typically only one lumen for conveying fluid to inflate and deflate the balloon. The distal neck of the balloon may be directly bonded to the guidewire, or the neck may be bonded to a rotatable sleeve, as shown in U.S. Pat. No. 5,279,560. To bond the balloon neck directly to the guidewire, it is necessary to first apply a bonding tube of opaque thermoplastic polymer to the desired location on the guidewire. In the latter case, either the sleeve may be made of opaque thermoplastic polymer, or an opaque bonding tube may be applied thereto.

Balloon 30 is shown in inflated condition, and when deflated, dilating portion 35 and end cones 37 will collapse and wrap around underlying catheter shaft 20. In this deflated condition, catheter 10 is advanced or drawn back through sometimes tortuous passageways in an effort to place balloon 30 inside the narrowing to be treated. This movement through curved vessels may challenge the flexibility of the distal portion of the catheter, especially in the areas where balloon necks 39 are attached to shaft 20. The balloon neck joints contribute additional stiffness to the assembly regardless of whether the joints are made with adhesive or thermal bonding. Therefore, it is desirable to make the joints as axially short as possible to minimize this effect.

The joints between necks 39 and shaft 20 must not only retain the balloon on the shaft, but they must also hold substantial hydraulic pressure during inflation of the balloon. For example, a coronary dilatation balloon most commonly measures 2.5 mm (0.098 inch) in diameter at the dilating portion, and is typically mounted onto a catheter shaft having a distal outer diameter of about 0.61 mm (0.024 inch). Such a balloon may have a designed burst pressure of 12 bars (174 p.s.i.) to 20 bars (290 p.s.i.) or more.

In accordance with the present invention, balloon neck 39 is welded to catheter shaft using energy in the red and near-infrared range. The preferred source of energy is a laser beam having the following characteristics: a wavelength of 630–1580 nm; a spot size of approximately 580 microns (0.023 inches) in diameter; and a power level of approximately 0.6–0.8 watts. The preferred generator of red and near-infrared energy can be either a continuous ND:YAG laser, or a low power diode laser. To heat the joint area, the laser beam is transmitted radially into the assembly through balloon neck 39 and impinging on shaft 20. Neck 39, and typically entire balloon 30, are formed from a thermoplastic polymer that is transparent or translucent to red and near-infrared energy so that there is little or no absorption of energy as it passes through the neck. Consequently, no part of balloon neck 39 is heated directly by the laser beam. The preferred balloon polymer is polyurethane block amide copolymer, although other materials such as nylon (polyamide) have also been shown to work in the invention. In catheter shaft 20, at least the distal section is made from a thermoplastic polymer that is opaque to red and near-infrared energy so that it absorbs the laser beam and is directly heated thereby. As the outer surface of shaft 20 is heated by the laser beam, heat is conducted to surrounding neck 39 until materials of both members melt and mix. It should be noted that the duration and power lever of the process are adjusted such that melting occurs only in a cylindrical zone that includes the annular interface between neck 39 and shaft 20. After the polymers melt and mix sufficiently, the laser beam is turned off to allow the materials to cool and form a solid weld joint.

Preferably, the portion of catheter shaft 20 that includes the area for welding balloon neck 39 is made from a multilayer polymeric coextrusion wherein only the outer layer needs to be opaque to red and near-infrared energy. Coextrusion offers a variety of combinations in material choices for the catheter shaft to obtain desired properties such as flexibility, balloon joint strength, and low friction for the inner layer. The preferred polymer for the catheter shaft, especially for the outer layer to be welded, is nylon 12 polyamide filled with carbon black to render it opaque to red and near-infrared energy. The preferred combination of materials in a coextruded catheter shaft in accordance with the invention includes an outer layer of black nylon 12, an inner layer of HMWHDPE (high molecular weight high density polyethylene), and an intermediate tie layer of Bynel®, a modified ethylene vinyl acetate adhesive resin available from E. I. du Pont de Nemours and Company, Wilmington, Del.

The annular weld between balloon neck 39 and shaft 20 is preferably formed by rotating the balloon catheter assembly around the central axis of the desired weld joint while the laser beam is directed to a site on balloon neck 39 approximately 4 mm (0.16 inches) from the base of balloon cone 37. The location of the weld from the balloon cone base is not limited. The weld can be placed at the balloon weld or any desired distance from the balloon cone base. With a laser spot size of 580 micron (0.023 inches) in diameter, a weld joint is produced that is slightly longer than the diameter of the spot size.

Figure 6:
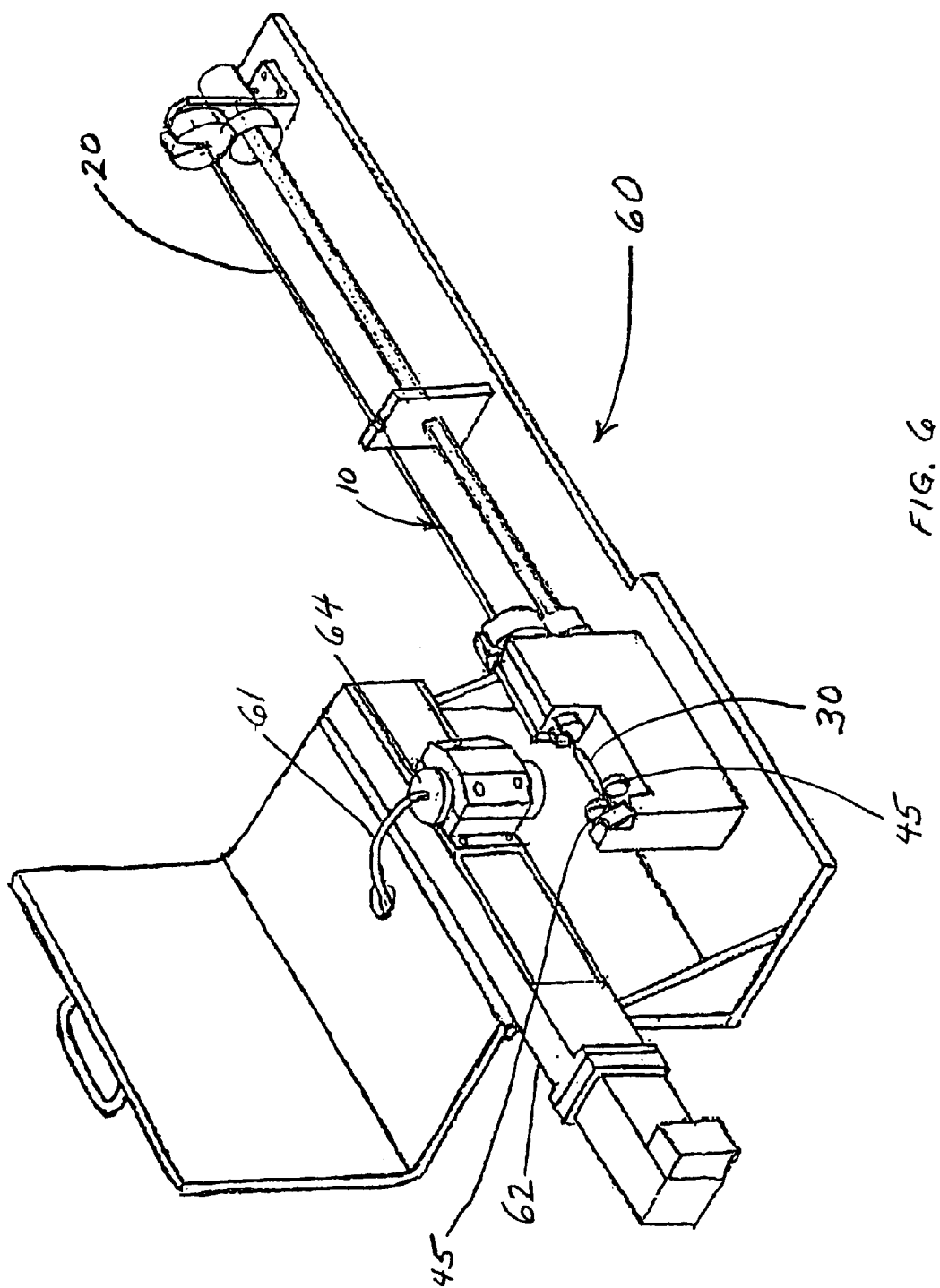
FIG. 6 is an isometric view of welding equipment used in the process of the present invention.

If a longer, stronger annular weld is desired, a short, helical path may be followed by the laser beam. Preferably, the helical path of the beam is generated by rotating the balloon catheter assembly about the central axis of the desired weld joint while the laser source traverses parallel to the joint axis. The preferred equipment to create the helical weld path is shown in FIG. 6 and will be discussed below. Other processes may be used to achieve a relative helical motion between the balloon catheter assembly and the laser beam, such as simultaneously rotating and translating the balloon catheter assembly beneath a fixed laser beam, or rotating and translating the laser beam around a fixed catheter assembly.

Figure 3:
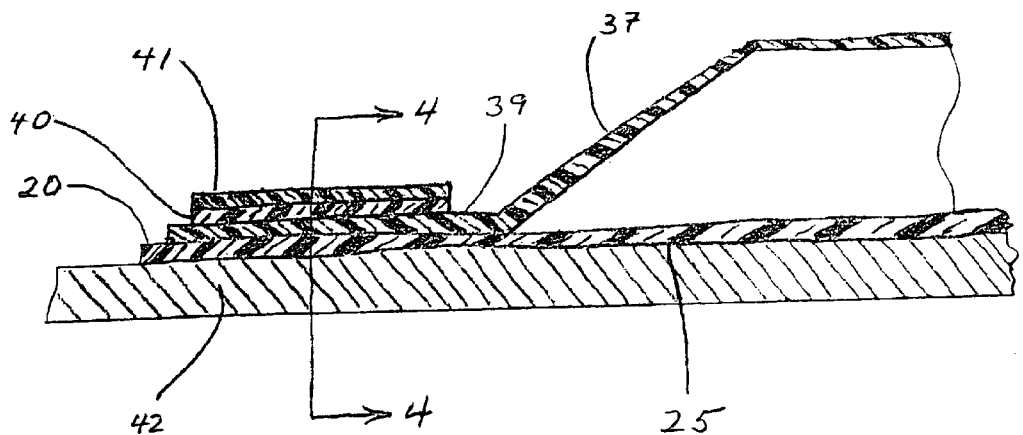
FIG. 3 is a longitudinal quarter-sectional view of a balloon catheter with compression tubes mounted over the balloon neck and a mandrel inserted into the catheter during a welding process of the present invention.
Figure 4:
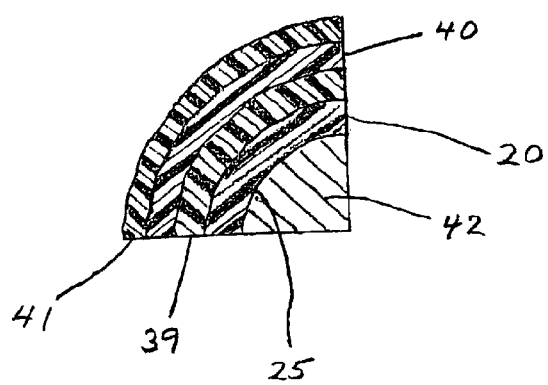
FIG. 4 is a cross-sectional view of the catheter shown in FIG. 3 taken along line 4—4.

FIG. 3 shows balloon catheter 30 of the present invention, assembled for through-transmission welding of a portion of neck 39 to a distal section of shaft 20. Neck 39 and shaft 20 are cylindrical and fitted closely together to provide an interface for welding. During the process of the invention, wire mandrel 42 is inserted into guidewire lumen 25 to support the tubular components being welded together. In this way, mandrel 42 may act as an axle, the catheter assembly rotating with or around it.

Optionally, the weld area may also have placed around it a section of shrink tubing 40 which is transparent or translucent to the red and near-infrared energy of the welding beam. Hot air may be applied to shrink tubing 40 so that it applies compression forces to the weld joint, holding balloon neck 39 and shaft 20 together, and helping to maintain the components in the desired cylindrical shape. Shrink tubing 40 also acts as an insulator to retain heat in the joint during welding. During the welding process, tubing 40 attempts to shrink due to heat conducted to it from the weld interface, where energy is absorbed by opaque shaft 20. This conduction heat is sufficient to shrink tubing 40, but it is too low to melt balloon neck 39. Instead of using hot air, a helical pass of the laser beam set to a reduced power may be used to shrink tubing 40 around the weld joint. Then, a second pass may be performed promptly over the joint to complete the weld, taking advantage of the compression forces and elevated joint temperature that were created during the first pass. A suitable piece of shrink tubing 40 may be made of polyester or preferably, a polyolefin such as polyethylene, and the tubing has an inside diameter that is close to the outside diameter of balloon neck 39.

In a further alternative to the above process of the invention, shrink tube 40 may also have placed around it a snug-fitting elastomeric tube 41, which is transparent or translucent to the red and near-infrared energy of the welding beam. In this second alternative process, elastomeric tube 41 acts as a heat sink to allow higher power to be applied to the weld, and also applies compression force in addition to that applied by shrink tubing 40. Silicone tubing has been found to be suitable for the elastomeric tube used in the process of the invention.

Figure 5:
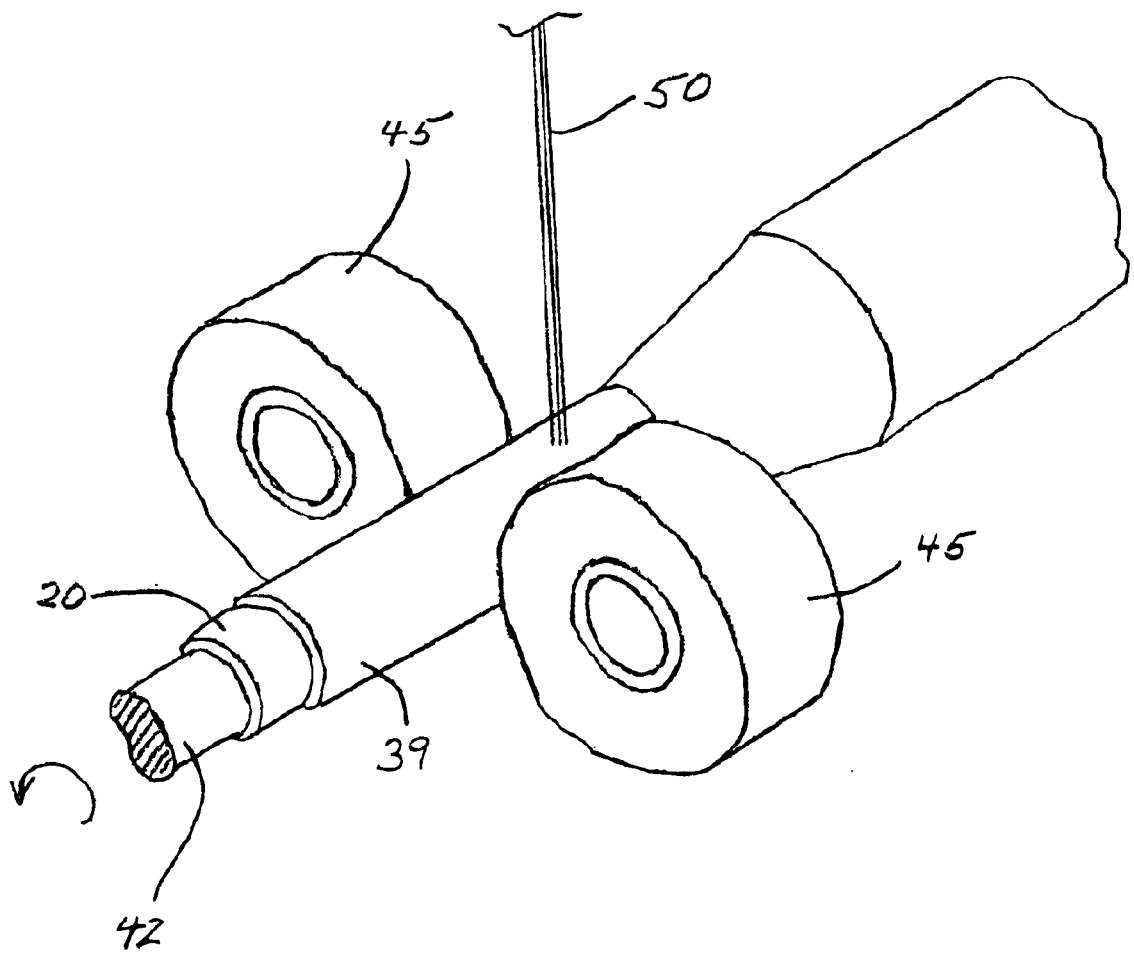
FIG. 5 is an isometric view of the distal portion of a balloon catheter with compression rollers used optionally during the welding process of the present invention.

FIG. 5 shows another alternative to the process of the invention, wherein one or more external rollers 45 apply light compression force to balloon neck 39 as the catheter assembly rotates beneath laser welding beam 50. Rollers 45 may be substituted for the compression sleeves such as shrink tube 40 and elastomeric tube 41, which may be time-consuming to remove after welding. During the welding process, rollers 45 cool the outer surface of balloon neck 39, keeping the outermost balloon neck material from melting while the inner materials melt. Thus, the outer material holds the molten inner material together. Furthermore, rollers 45 provide gentle pressure during welding, in place of the compression sleeves, thus ensuring intimate contact and mixing of the molten materials. When a pair of rollers 45 are used, as shown in FIG. 5, both of their central axes lie in a plane that also passes through the central axis of the assembly to be welded. The rollers may be made from metals, such as stainless steel or brass.

An alternative when using rollers 45 during the welding process is to form a texture in the weld joint. For example, annular corrugations, which are not shown in metal rollers 45, can form corresponding annular corrugations in welded balloon neck 39, thus improving flexibility in that part of the catheter.

A piece of equipment capable of performing through-transmission welding according to the present invention is shown as fixture 60 in FIG. 6. Balloon 30 is shown placed on catheter shaft 20, with the assembly mounted for rotation about its axis in fixture 60. The distal end of catheter 10 is inserted in fixture 60 beneath lens 64, and between two optional rollers 45. Optical fiber 61 brings energy from the laser generator, not shown, to lens 64, which may be translated parallel to the catheter axis by motorized slide 62.

When practicing the present invention to fabricate a coronary balloon angioplasty catheter having the optional cylindrical weld with a helical laser path, fixture 60 has the following operating characteristics: catheter 10 rotational speed: approximately 400 rpm; traverse distance of lens 64: about 1.25 mm (0.049 inches); traversing speed of lens 64: about 127 mm (5 inches) per minute. At the end of the welding time of approximately 6 seconds, the energy source is turned off, the assembly is allowed to cool and solidify in the balloon neck joint, and the compression tubes, if used, are removed.

Thus, in summary, the process of the invention involves first selecting a catheter shaft having a thermoplastic material opaque to red and near-infrared light. Next, the balloon is selected to have a thermoplastic material transparent or translucent to near-visible light. The balloon is then mounted on the catheter shaft. Red and near-infrared laser light is then applied to the balloon neck and underlying catheter shaft with relative rotary motion. Lastly, the assembly is cooled.

While only a few embodiments have been illustrated and described in connection with the present invention, various modifications and changes in both the apparatus and method will become apparent to those skilled in the art. All such modifications or changes falling within the scope of the claims are intended to be included therein.

We claim:

1. A process for forming a heat weld between a catheter shaft and a surrounding balloon comprising the steps of:
    selecting an elongate catheter shaft having a distal portion fanned of thermoplastic polymeric material that is opaque to red and near-infrared light;
    selecting a balloon having at least one neck formed of thermoplastic polymeric material that is transparent or translucent to red and near-infrared light;
    making an assembly by placing the balloon around the distal shaft portion such that the balloon neck is fitted in close uniform contact with the distal portion of the shaft;
    selecting a low power laser source of red and near-infrared light;
    causing relative rotation between a beam of light from the laser source and the assembly;
    applying light from the laser source as a nondispersed laser beam through the balloon neck to the underlying distal shaft portion such that polymer melting occurs in a cylindrical region including adjacent parts of the neck and shaft portions; and
    permitting the cylindrical region to cool and solidify into a joint between the catheter shaft and the balloon.

2. The process of claim 1 further including the step of, before applying the laser light, applying over the balloon neck a section of heat shrinkable tubing that is transparent or translucent to red and near-infrared light.

3. The process of claim 2 further including the step of applying over the heat shrinkable tubing a section of tight fitting elastomeric tubing that is transparent or translucent to red and near-infrared light.

4. The process of claim 1 wherein relative rotation is provided by rotating the balloon and shaft assembly relative to a fixed laser beam, and wherein the balloon neck and underlying shaft rotate between at least two rollers which apply pressure to the combined neck and shaft during welding.

5. The process of claim 4 wherein the contact surfaces of the rollers are textured so that a corresponding textured surface is applied to the combined neck and shaft during the welding process.

6. The process of claim 1 wherein the opaque portion of the distal shaft is the outer layer of a multiple layer coextrusion.

7. The process of claim 1 wherein the red and near-infrared light has a wavelength of no more than about 1580 nanometers.

8. The process of claim 7 wherein the red and near-infrared light source is a Nd:YAG laser.

9. The process of claim 7 wherein the red and near-infrared light source is a low power diode laser.

10. The process of claim 1 wherein the low power is in the range of 0.6–0.8 watts.

* * * * *